United States Patent [19]

Seamark et al.

[11] Patent Number: 4,738,679
[45] Date of Patent: Apr. 19, 1988

[54] VETERINARY IMPLANT

[75] Inventors: Robert F. Seamark, Beulah Park; David J. Kennaway, Prospect; Eugene Dunstan, Naracoorte, all of Australia

[73] Assignee: Gene Link Australia Limited, South Melbourne, Australia

[21] Appl. No.: 783,954

[22] PCT Filed: Jan. 26, 1985

[86] PCT No.: PCT/AU85/00013

§ 371 Date: Oct. 15, 1985

§ 102(e) Date: Oct. 15, 1985

[87] PCT Pub. No.: WO85/03227

PCT Pub. Date: Aug. 1, 1985

[30] Foreign Application Priority Data

Jan. 26, 1984 [AU] Australia ............... PG3361

[51] Int. Cl.$^4$ .............................................. A61K 9/22
[52] U.S. Cl. ............................. 604/892.1; 604/891.1
[58] Field of Search ................. 514/416; 530/331; 604/890, 891, 892; 424/94; 623/66, 11

[56] References Cited

U.S. PATENT DOCUMENTS

| | | | |
|---|---|---|---|
| 3,428,729 | 2/1969 | Anderson et al. | 424/19 |
| 3,991,750 | 11/1976 | Vickery | 604/891 |
| 4,163,011 | 7/1979 | Orts | 530/331 |
| 4,322,398 | 3/1972 | Reiner et al. | 424/19 |
| 4,346,709 | 8/1982 | Schmitt | 604/891 |
| 4,576,604 | 3/1986 | Guittard et al. | 604/890 |

FOREIGN PATENT DOCUMENTS

| | | |
|---|---|---|
| 78305/81 | 6/1982 | Australia . |
| 51657/79 | 7/1983 | Australia . |
| 2271832 | 2/1975 | France . |

OTHER PUBLICATIONS

Kennaway et al., Endocrinology, 110 (6), 2186-2188 (1982).

Primary Examiner—Richard J. Apley
Assistant Examiner—Alan W. Cannon
Attorney, Agent, or Firm—Merchant, Gould, Smith, Edell, Welter & Schmidt

[57] ABSTRACT

A method of regulating the reproductive functions of animals, preferably domesticated ruminants, and veterinary implants for use in such a method are provided. The veterinary implant tablet comprises about 2-15% by weight of a fatty acid salt compression binder, about 25-50% by weight of a directly compressible vehicle selected from the group consisting of calcium phosphate and derivatives thereof, about 1-5% by weight of a granulating agent, and an amount of melatonin effective to maintain blood melatonin at, or above, a natural nighttime level of an animal to be treated for a period of time effective to accelerate an onset of breeding activity in mature animals or to delay an onset of puberty in prepubescent animals. The implant tablet provides a substantially continuous release rate of melatonin so as to maintain blood melatonin at, or above, the stated level. A method for preparing such a veterinary implant tablet is also described. A method of modifying the seasonal breeding activity of animals is also provided which comprises administering to an animal to be treated the disclosed veterinary implant tablet.

9 Claims, No Drawings

VETERINARY IMPLANT

This invention relates to a method of regulating the reproductive functions of animals, particularly domesticated ruminants, and to veterinary implants for use in such a method.

In our earlier Australian patent application No. 78305/81 there is described a method of artificially mimicking changing photoperiod and thus the seasonal breeding activity of sheep and goats by the judicious feeding of melatonin or other related indoles or indole derivatives.

The role of seasonal environmental factors, in particular the photoperiod, in determining the breeding period of sheep is well established. Under natural conditions the shortening of day length as summer leads to autumn is the main trigger to the reproductive system to commence ovarian cyclicity. Our previous application shows that melatonin treatment can mimick the effects of short day length on ewes, such that the breeding season is advanced and basal prolactin levels are depressed.

In the earlier patent specification this was achieved by feeding the animal with food containing melatonin or related indole or indole derivatives for a period of time sufficient for the animal to commence cyclic ovarian activity. This was achieved by absorbing the melatonin in food pellets, and in this way 2 mg of melatonin per day was fed to each animal.

This however requires the daily feeding of the pellets to the animals for a period of three to six weeks.

It is therefore an object of the present invention to overcome, or at least alleviate, some of the difficulties related to the prior art.

Accordingly, in a first aspect, the present invention provides a veterinary implant including an effective amount of (a) an active ingredient selected from melatonin, related indoles and derivatives thereof, or mixtures thereof and (b) a veterinarily acceptable carrier or excipient selected to provide, in use, in combination with the active ingredient (a), a generally continuous release rate of active ingredient sufficient to maintain blood melatonin, or its equivalent, at, or above, natural night time level. For domesticated ruminants such as sheep and goats this level is approximately 100 pg/ml. Preferably the veterinary implant according to the present invention is formed by compression.

In a further aspect the present invention provides a method of modifying the seasonal breeding activity of animals which method includes inserting a veterinary implant of the type described herein into an animal to be treated.

The modification of breeding activity may be such as to accelerate the onset of breeding activity or delay the onset of puberty. In delaying the onset of puberty the onset of the breeding season of the animal may be altered. This effect may continue for an extensive period e.g. 2-4 years.

By the term "melatonin" as used herein, we mean the active ingredient in the veterinary implant selected from melatonin, related indoles and derivatives thereof or mixtures thereof.

In the following description reference will be made to the ethicacy of the veterinary implants in sheep, goats and cattle. It should be understood, however, that such animals are mentioned for illustrative purposes only and the veterinary implant is applicable to animals generally. The veterinary implant may be applied to animals including sheep, goats, horses, cattle, deer, buffalo, pigs, ferrets, mink, fox, sable, ermine, bear, camels, lamas and the like. The veterinary implants may further be applied to the regulation of seasonal breeding activity in birds, reptiles, including alligators, crocodiles, turtles and snakes, and fish including sturgeon, trout, salmon and eels.

As discussed below, initial experiments exploring the effects of continuous melatonin administration were carried out utilizing implants in the form of melatonin filled silastic sachets. Whilst these implants were useful for experimental purposes, such implants are deficient in a number of aspects. Firstly, they are difficult and therefore expensive to manufacture and are therefore impractical for large scale application. Further, their size makes their introduction into an animal and subsequent removal a difficult surgical technique. It would be a significant advance in the art if a veterinary implant could be provided which overcomes, or at least alleviates, some of these difficulties.

In a preferred aspect the present invention provides a veterinary implant as described above, further including (c) an effective amount of a compression lubricant.

The lubricant may be present in an amount of approximately 1 to 30% by weight, preferably 1 to 5% by weight based on the total weight of the veterinary implant. The lubricant may be a food grade lubricant. The lubricant may be a natural food source lubricant. The lubricant may be derived from vegetable oil. The lubricant may be a lubricant of the type sold under the trade designation "LUBRITRAB" and available from Edward Mendell Co. Inc., New York, U.S.A.

According to a still further aspect of the present invention the veterinary implant may further include (d) an effective amount of a binder.

The binder may be present in amounts of from approximately 1 to 30% by weight based on the total weight of the veterinary implant. The binder may be present preferably in amounts of approximately 2 to 15% by weight.

The binder may be a fatty acid salt. The fatty acid salt may be an alkaline earth metal salt. A stearic acid salt is preferred. Zinc stearate or magnesium stearate may be used.

As stated above, the veterinary implant according to the present invention in a preferred aspect may be formed by compression. The active ingredient (a) and the veterinarily acceptable carrier (b) may be intimately mixed and then compressed. The veterinary implants may be compressed in a tablet press.

In a preferred form the present provides a veterinary implant wherein the implant is formed by direct compression. In this form the veterinarily acceptable carrier or excipient may include approximately 25 to 50% by weight based on the total weight of the veterinary implant of a directly compressible vehicle selected to control the release rate of active ingredient. The directly compressible vehicle may be an acid salt. The acid salt may be a phosphate salt. The directly compressible vehicle may be an alkaline earth metal salt. A calcium phosphate is preferred. An hydrated acid salt may be used. A dibasic calcium phosphate dihydrate is preferred. The acid salt may be a calcium phosphate of the type sold under the trade designation "ENCOM- PRESS" and available from Edward Mendell Co. Inc., New York, U.S.A.

The acid salt is preferably present in an amount of from approximately 30 to 40% by weight based on the total weight of the veterinary implant.

Accordingly, in a further aspect of the present invention there is provided a veterinary implant of the type described above wherein the implant is formed utilizing a granulation and compression method. In this form, the veterinarily acceptable carrier (b) includes an effective amount of a granulation agent selected from a compound or a high molecular weight compound or mixtures thereof.

The granulating agent may be present in amounts of from approximately 1 to 30% by weight preferably 1 to 5% by weight based on the total weight of the veterinary implant. The granulating agent may be selected from a cellulose compound or other high molecular weight compound or mixtures thereof. The cellulose compound or high molecular weight compound may be a water insoluble compound. The cellulose compound may be selected from ethyl cellulose, methyl cellulose, cellulose acetate or derivatives thereof. Cellulose acetate phthalate or a compound sold under the trade designation "METHOCEL" may be used. As the high molecular weight compound, vinyl polymer may be used. Polyvinyl pyrrolidone is preferred. Alternatively, or in addition, naturally occurring high molecular weight compounds, such as the waxes, for example beeswax, may be included.

The polyvinyl pyrrolidone utilized in the veterinary implants according to the present invention may be selected from a range of polyvinyl pyrrolidone of varying molecular weights and available from GAF Corporation of the U.S.A. under the trade designation "PLASDONE" including Plasdone K-29/32 and Plasdone K-90. Plasdone K-29/32 has a volume average molecular weight of approximately 38,000. K-90 has a volume average molecular weight of approximately 630,000.

The molecular weight of the polymer affects the following properties of the material.
(1) Viscosity in solution.
(2) Adhesion properties.
(3) Rate of solution (dissolution).
(4) Rate of absorption and excretion.

As the K-value of Plasdone excipient increases, values for the first two properties listed above increase while the last two decrease.

Where the granulation method is a wet granulation method, the granulating agents may be present in a solution or suspension. A solution or suspension in alcohol may be used.

In accordance with a further aspect of the present invention there is provided a method of preparing a veterinary implant as described above, which method includes
(1) providing an effective amount of
  (a) an active ingredient selected from melatonin related indoles and derivatives thereof or mixtures thereof and
  (b) a veterinarily acceptable carrier or excipient selected to provide, in combination with the active ingredient (a), in use a generally continuous release rate of active ingredient sufficient to maintain blood melatonin or its equivalent at, or above, natural night time levels;
(2) mixing the components of step 1 and
(3) compressing the mixture under a pressure and temperature sufficient to form a veterinary implant.

The components of step 1 may optionally include a binder and/or lubricant as described above. The components may be mixed together intimately in any suitable container.

The mixture is then subjected to a compression step. Compression may be carried out at a temperature in the range of from room temperature to approximately 90° C. The temperature selected will be dependent upon the stability of the active ingredient and the veterinarily acceptable carrier or excipient selected. The compression may be conducted under pressures of up to several hundred bar, for example 5 to 1200 bar. Preferably compression is undertaken with pressures of approximately 1 to 800 bar. The veterinary implant may be compressed into any suitable form. For example, the veterinary implant may be in the form of a tablet, a bead, a cylinder, a rod or a plate. A tablet form is preferred. In this form, a standard tablet press may be used.

In a still further aspect of the present invention there is provided a method of preparing a veterinary implant which includes
(1) providing an effective amount of (a) an active ingredient selected from melatonin related indoles and derivatives thereof or mixtures thereof and (b) a granulating agent selected from a cellulose compound or a high molecular weight compound;
(2) mixing the components of step (a) for a time sufficient to form an intimate mixture thereof;
(3) subjecting the mixture to the granulating step and
(4) compressing the granulated mixture under a pressure and temperature sufficient to form a veterinary implant.

Where the granulation step is a wet granulation step, the veterinarily acceptable carrier (b) may be provided in the form of a solution. An alcohol solution may be used.

The implants may be individually loaded into a separate chamber of a plastic cartridge. The plastic cartridges may be placed into a "gun" and the implant delivered subcutaneously through a large bore needle.

It has been found that implants prepared utilizing the above described methods may be cheaply and efficiently manufactured and lend themselves to mass production techniques. The implants so formed have been found to release the active ingredient at a generally continuous rate sufficient to maintain blood melatonin or its equivalent at, or above, the natural night time levels of the subject animal. Thus the veterinary implants are suitable for use in the reproductive regulation methods according to the present invention.

Accordingly, in a further aspect of the present invention there is provided a method of modifying the seasonal breeding activity of animals which method includes inserting into an animal to be treated a veterinary implant including an effective amount of (a) an active ingredient selected from melatonin, related indoles and derivatives thereof, or mixtures thereof and (b) a veterinarily acceptable carrier or excipient selected to provide, in use, in combination with the active ingredient sufficient to maintain blood melatonin, or its equivalent, at, or above, natural night time level.

Preferably the blood melatonin, or its equivalent, is maintained at or above a level of approximately 100 pg/ml.

The animal to be treated may be a mature animal and the seasonal breeding activity is modified by accelerating the onset of the breeding season.

The animal to be treated may be a pre-pubescent animal and the seasonal breeding activity is modified by delaying the onset of puberty and thus the onset of the breeding season is altered over a number of years.

In general, the animal to be treated will be a female. Particularly significant results are achieved when the animals treated are maiden females. However, alternatively or in addition the male of the species may be treated. This is preferable for deer and goats, and to a lesser extent, sheep.

The present invention will now be more fully described with reference to the accompanying examples. It should be understood, however, that the examples are illustrative only and should not be taken in any way as a restriction on the generality of the invention described above.

EXAMPLES

EXAMPLES 1 TO 17

Veterinary implants according to the present invention are prepared in utilizing the ingredients and methods of manufacture as specified below. In each example the ingredients were intimately mixed together and, where stated, wet granulated utilizing an alcohol solvent.

The wet granulation step consists of moistening the mixture of active ingredient and, if required, diluent with the granulating liquid comprising the binder in solution in water, alcohol, or mixture of those two, or any other acceptable liquid to moisten and bind the powders together by causing the particles to adhere to each other. The wet mass produced by mixing the liquid with the solid should have a doughlike consistency so that a handful can be formed into shape without crumbling. When pressed into a ball with the hands and broken in half, it should give a clean fracture without sticking or crumbling. If the mass has a tendency to stick or not break clean, the granulation is usually too wet. If the mass crumbles or breaks into pieces it is too dry.

For the purpose of granulating melatonin the granulating agents used were dissolved in ethanol 96%. To form the granules the wet mass was passed through a 12 mesh (1.4 mm) sieve and allowed to dry at room temperature. The dry granules were then passed through a 25 mesh (600 um) sieve prior to mixing with the lubricant.

The implants are manufactured from the above powders using standard tabletting techniques.

The mixtures or granulated mixtures were then compressed to form a veterinary implant in tablet form utilizing a tablet press. Each of the implants function satisfactorily but superior results were achieved utilizing the wet granulation and compression method. The implant manufactured according to example 7 was also found to be superior as a continuous blood melatonin was maintained above 100 pg/ml for a longer period than with other implants. The reduced melatonin implant manufactured according to example 15 was found to be effective in modification of breeding activity with substantially reduced melatonin contents.

MELATONIN IMPLANTS
Note: All weights of Ingredients in mg

| | 1 | 2 | 3 |
|---|---|---|---|
| Melatonin | 20 | 20 | 10 |
| P.V.P. (10%) | 1 | 1.2 | 1 |
| Beeswax | 1 | 1 | 1 |
| Dibutylphlate | 0.1 | — | 0.1 |
| Lubritab ® | 1 | 1 | — |
| Zn Stearate | — | — | 1 |
| Encompress ® | — | — | 5 |
| Method of Manufacture: Wet Granulation and Compression | | | |

| | 4 | 5 | 6 |
|---|---|---|---|
| Melatonin | 10 | 10 | 15 |
| Encompress ® | 5 | 5 | 5 |
| Lubritab ® | 1 | 1 | 0.8 |
| Mg. Stearate | — | 0.4 | — |
| Method of Manufacture: Direct Compression | | | |

| | 7 | 8 |
|---|---|---|
| Melatonin | 20 | 20 |
| P.V.P. K (5%) | 0.2 | 0.3 |
| Cellulose Acetate Phthalate | — | 2 |
| Lubritab ® | 0.3 | 0.3 |
| Method of Manufacture: Wet Granulation and Compression | | |

| | 9 | |
|---|---|---|
| Melatonin | 20 | |
| Methocel A15C Prem | 2 | granulate with alcohol |
| Lubritab ® | 0.3 | |
| Method of Manufacture: Wet Granulation and Compression | | |

| | 10 | | 12 |
|---|---|---|---|
| Melatonin | 20 | | 20 |
| P.V.P. K-90 10% qs to (alcohol) granulate | 0.64 | qs to granulate twice | 1.11 |
| Lubritab ® | 0.64 | | 0.64 |
| Method of Manufacture: Wet Granulation and Compression | | | |

| | 11 | | 13 |
|---|---|---|---|
| Melatonin | 20 | | 20 |
| Ethylcellulose 10% qs to (alcohol) granulate | 0.59 | qs to granulate twice | 1.09 |
| Lubritab ® | 0.64 | | 0.62 |
| Method of Manufacture: Wet Granulation and Compression | | | |

| | 14 |
|---|---|
| Melatonin | 20 |
| P.V.P. K-90 10% qs to (alcohol) granulate | 0.64 |
| Ethylcellulose 10% qs to (alcohol) granulate | 0.49 |
| Lubritab ® | 0.64 |
| Method of Manufacture: Wet Granulation and Compression | |
| Implants with Reduced Melatonin Content | |

| | 15 | 16 | 17 |
|---|---|---|---|
| Melatonin granulate with PVP-K-90 | 12.5 | 5 | 2 |
| Encompress ® | 12.9 | 26.1 | 31.5 |
| Lubritab ® 3% | 0.7 | 1.0 | 1.1 |
| implant weights | 26.6 | 32.4 | 34.5 |
| Method of Manufacture: Wet Granulation and Compression | | | |

EXAMPLE 18

Experiments exploring the effects of continuous melatonin administration were carried out on ten Border Leceister×Merino ewes. The ewes were housed in an animal house under a lighting regime simulating the normal change in photoperiod occurring at that time of year. To provide a continuous source of melatonin subcutaneous implants were prepared. These implants were in the form of melatonin filled sachets constructed from two 25 mm square silasticmedical grade sheets (0.125 cm thick: Dow Corning, Midland, Mich. U.S.A.) with edges cemented together with silastic glue. Invitro tests showed that implants of this size released between 100–150 ug melatonin per day with buffered protein (1% albumin) solution; the amount needed, as calculated from production rate studies, to maintain blood melatonin continuously at nightime levels. Five ewes were implanted subcutaneously with melatonin filled sachets and 5 with empty sachets as controls.

Blood samples (19×20 min), taken 5 days before and 17 and 30 days after the subcutaneous placement of the sachets, showed that in the treated animals blood levels of melatonin were maintained at 100–180 pg/ml in the controls. After 17 days of treatement blood prolactin levels had decreased dramatically in the melatonin group 11±ng/ml (±SD) compared with 134±29 ng/ml in the control group. Analysis of single daily samples indicated that this decrease had occurred as early as 7 days after implantation.

The results in sheep indicated that constant melatonin administration exerted a similar effect of plasma prolactin levels to daily oral administration (Aust. Patent Application No. 78305/81) but that the effect was achieved more rapidly i.e. approx. 7 days compared to approx. 20-30 days with the oral route.

This result was unexpected as according to previous experiments mainly carried out with laboratory rodents continuous melatonin administration should have had consequences similar to long day length and thus opposite to those obtained with daily administration. Similar results were achieved utilizing veterinary implants as preferred in examples 1 to 17.

EXAMPLE 19

In a further experiment beeswax and melatonin were mixed at 140° C. and drawn into polyethylene tubing of either 2.2 mm or 2.0 mm diameter. Various proportions of melatonin/beeswax were used e.e. 1:24, 3:22, 10:15. 4 mm lengths of the material were then injected intramuscularly into an ear, or subcutaneously into the face or back of a group of wethers. Blood samples were then taken weekly for 8 weeks and blood assayed for melatonin. Using this approach it was shown that beeswax implants (10:15 aMT:BW, total length 8 mm diameter 2.2 mm) when injected into an ear muscle produced stable blood levels of melatonin excess of 100 pg/ml for up to 8 weeks.

Thus according to the invention it has been found that constant melatonin availability in a sheep (which is a short day breeding species) has consequences similar to short day length that is blood prolactin decreases. This is in contrast to results from long day breeding species like the hamster and which constant melatonin availability has consequences similar to long day length.

It has also been found that melatonin can influence the age at which puberty occurs in ewe lambs. The age at which puberty occurs in ewe lambs is determined in part by the season of birth and in part by prevailing photoperiod conditions. Thus animals born in autumn or winter have puberty delayed until the following autumn, corresponding to the time of onset of puberty of younger lambs.

By the use of melatonin implants as in examples 1 to 17, the time of the onset of puberty and the long term seasonality of the ewe can be adjusted as indicated by an experiment in which five ewe lambs born in April 1981 to pinealectomized ewes implanted s.c. with melatonin sachets and 6 ewe lambs implanted with empty sachets.

Puberty (determined by weekly progesterone analysis) was delayed ($P<0.05$) in 4 of the 5 melatonin-treated ewe lambs; means pubertal age of ewes with empty implants was 44 weeks of age compared to 45, 63, 72, >72, >72 weeks of age for the melatonin-treated animals. The seasonal difference in the timing of the onset of breeding activity again occured during Spring in the melatonin treated animals as opposed to late Summer/Autumn in the ewes, with treated empty implants.

Hence according to the invention not only can the ovarian activity be brought forward in time for early breeding from ewes, but also that puberty and season adjusted.

The claims defining the invention are as follows:

1. A veterinary implant tablet comprising:
   (a) about 2 to 15% by weight based on the total weight of said tablet of a fatty acid salt compression binder;
   (b) about 25 to 50% by weight based on the total weight of said tablet of a directly compressible vehicle selected from the group consisting of calcium phosphate and derivatives thereof;
   (c) about 1 to 5% by weight based on the total weight of said tablet of a granulating agent; and
   (d) an amount of melatonin effective to maintain blood melatonin at, or above, a natural nighttime level of an animal to be treated for a period of time effective to accelerate an onset of breeding activity in mature animals or to delay an onset of puberty in prepubescent animals; wherein said implant tablet provides a substantially continuous release rate of melatonin so as to maintain blood melatonin at, or above, said level for said period of time.

2. The veterinary implant tablet of claim 1 wherein the blood melatonin is maintained at a level at, or above, about 100 pg/ml, and the animal to be treated is a domesticated ruminant.

3. The veterinary implant tablet of claim 1 wherein the granulating agent is selected from the group consisting of ethyl cellulose, methyl cellulose, cellulose acetate, cellulose acetate phthalate, vinyl polymers, waxes and mixtures thereof.

4. The veterinary implant tablet of claim 3 wherein the granulating agent includes a polyvinyl pyrrolidone having a molecular weight selected to provide an effective release rate of melatonin.

5. A method for preparing a veterinary implant tablet which method comprises:
   (1) providing
      (a) about 2 to 15% by weight based on the total weight of said tablet of a fatty acid salt compression binder;
      (b) about 25 to 50% by weight based on the total weight of said tablet of a directly compressible vehicle selected from the group consisting of calcium phosphate and derivatives thereof;
      (c) about 1 to 5% by weight based on the total weight of said tablet of a granulating agent; and
      (d) an amount of melatonin effective to maintain blood melatonin at, or above, a natural nighttime level of an animal to be treated for a period of time effective to accelerate an onset of breeding activity in mature animals or to delay an onset of puberty in prepubescent animals;
   (2) mixing the components of step 1; and
   (3) compressing the mixture under a temperature and pressure sufficient to form the veterinary implant tablet; wherein said tablet provides a substantially continuous release rate of melatonin so as to maintain blood melatonin at, or above, said level for said period of time.

6. A method of modifying the seasonal breeding activity of animals, which comprises administering to an animal to be treated a veterinary implant tablet comprising:
   (a) about 2 to 15% by weight based on the total weight of said tablet of a fatty acid salt compression binder;
   (b) about 25 to 50% by weight based on the total weight of said tablet of a directly compressible vehicle selected from the group consisting of calcium phosphate and derivatives thereof;
   (c) about 1 to 5% by weight based on the total weight of said tablet of a granulating agent; and
   (d) an amount of melatonin effective to maintain blood melatonin at, or above, a natural nighttime level of an animal to be treated for a period of time effective to accelerate an onset of breeding activity in mature animals or to delay an onset of puberty in prepubescent animals; wherein said implant tablet provides a substantially continuous release rate of melatonin so as to maintain blood melatonin at, or above, said level for said period of time.

7. The method of claim 6 wherein the blood melatonin is maintained at, or above, a level of about 100 pg/ml, and the animal to be treated is a domesticated ruminant.

8. The method of claim 7 wherein the animal is a mature animal and the seasonal breeding activity is modified by accelerating the onset of the breeding season.

9. The method of claim 5 wherein the animal is a pre-pubescent animal and the seasonal breeding activity is modified by delaying the onset of puberty.

* * * * *